(12) United States Patent
Burd

(10) Patent No.: US 11,045,495 B2
(45) Date of Patent: *Jun. 29, 2021

(54) METHOD OF IMPROVING BETA CELL FUNCTION USING A SUPPLEMENT

(71) Applicant: Lysulin, Inc., San Diego, CA (US)

(72) Inventor: John Burd, San Diego, CA (US)

(73) Assignee: Lysulin, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/414,747

(22) Filed: May 16, 2019

(65) Prior Publication Data

US 2019/0269723 A1 Sep. 5, 2019

Related U.S. Application Data

(60) Division of application No. 16/153,450, filed on Oct. 5, 2018, which is a continuation-in-part of application No. 15/817,574, filed on Nov. 20, 2017.

(60) Provisional application No. 62/581,573, filed on Nov. 3, 2017.

(51) Int. Cl.
| | |
|---|---|
| *A61K 33/30* | (2006.01) |
| *A61P 3/08* | (2006.01) |
| *A23L 33/175* | (2016.01) |
| *A61K 31/375* | (2006.01) |
| *A61K 31/13* | (2006.01) |
| *A23L 33/16* | (2016.01) |
| *A23L 33/15* | (2016.01) |

(52) U.S. Cl.
CPC .............. *A61K 33/30* (2013.01); *A23L 33/15* (2016.08); *A23L 33/16* (2016.08); *A23L 33/175* (2016.08); *A61K 31/13* (2013.01); *A61K 31/375* (2013.01); *A61P 3/08* (2018.01); *A61K 2300/00* (2013.01)

(58) Field of Classification Search
CPC ...... A61K 33/10; A61K 31/13; A61K 31/375; A23L 33/175; A23L 33/16; A23L 33/15; A61P 3/08
See application file for complete search history.

(56) References Cited

U.S. PATENT DOCUMENTS

| | | |
|---|---|---|
| 8,060,249 B2 | 11/2011 | Bear et al. |
| 2003/0082074 A1 | 5/2003 | Jurik et al. |
| 2004/0060859 A1 | 4/2004 | Seshimoto |
| 2007/0238770 A1 | 10/2007 | Gougoutas |
| 2008/0004507 A1 | 1/2008 | Williams |
| 2008/0014644 A1 | 1/2008 | Barasch |
| 2008/0027024 A1 | 1/2008 | Gahler et al. |
| 2013/0035563 A1 | 2/2013 | Angelides |
| 2014/0044828 A1 | 2/2014 | Mine |
| 2014/0227371 A1 | 8/2014 | Heath |
| 2014/0256806 A1 | 9/2014 | Tanaka |
| 2014/0363896 A1 | 12/2014 | Suzuki |
| 2015/0038453 A1 | 2/2015 | Hageman |
| 2015/0160218 A1 | 6/2015 | Demirci |
| 2015/0182483 A1 | 7/2015 | Goldberg |
| 2016/0263317 A1 | 9/2016 | Arefieg |
| 2017/0061823 A1 | 3/2017 | Cohen |
| 2017/0255758 A1 | 9/2017 | Washko |

FOREIGN PATENT DOCUMENTS

| | | |
|---|---|---|
| CN | 101642468 A1 | 2/2010 |
| CN | 102772215 | 11/2012 |
| CN | 104138469 | 1/2014 |
| WO | WO2004035074 A1 | 4/2004 |
| WO | WO2005123108 A1 | 12/2005 |
| WO | WO2008120797 A1 | 9/2008 |
| WO | WO2010017190 A1 | 2/2010 |
| WO | WO2011086507 A1 | 7/2011 |

OTHER PUBLICATIONS

Khayat, Y., "Anti-Glycation Supplements Part III (Glycation: Part II of II)." Perspectives on Health, Jan. 26, 2015 (Jan. 26, 2015), pp. 1-52. Retrieved from the internet: <https://yachonakhayat.wordpress.com/2015/01/26/anti-glycation-supplements-part-iii-glycation-part-ii-of-ii/> on Mar. 6, 2018 (Jun. 3, 2018). entire documents.

International Search Report and Written Opinion corresponding to International Application No. PCT/US2018/015587, dated Apr. 13, 2018.

International Search Report and Written Opinion corresponding to International Application No. PCT/US2018/015593, dated Mar. 26, 2018.

International Search Report and Written Opinion corresponding to International Application No. PCT/US2018/015589, dated Mar. 22, 2018.

Examine.com, "Zinc," published online: Nov. 1, 2016; obtained via Internet Archive Wayback Machine on Apr. 26, 2018.

National Institute for Health Research, "Point-of-Care Creatinine Testing for the Detection and Monitoring of Chronic Kidney Disease." NIHR Diagnostic Evidence Cooperative Oxford; Mar. 2014, p. 2 heading details of technology; p. 3, heading importance and table 1; p. 5, second paragraph.

Nova Biomedical, StatSensor Point-of-Care Whole Blood Creatinine and eGRF Testing, May 2008; [retrieved Mar. 8, 2918]. Retrieved from the Internet; <URL: http://novamed.dk/uf/30000-39999/38239/202711fdbd525ddc1c17d1ab983a44.pdf>; p. 2 photograph; p. 8, heading docking station.

(Continued)

*Primary Examiner* — Genevieve S Alley
(74) *Attorney, Agent, or Firm* — Sheppard Mullin Richter & Hampton LLP

(57) ABSTRACT

A method of improving beta cell function by using a supplement, the comprising: administering the supplement comprising lysine, zinc, and vitamin C to a user; monitoring an insulin resistance level before and after the supplement is administered in a bio-sample; and determining a change in a dose of the supplement based on the insulin resistance level found in the bio-sample.

4 Claims, 8 Drawing Sheets

(56) References Cited

OTHER PUBLICATIONS

Medtronic "Guardian Real-Time Continuous Glucose Monitoring System" 2006; (retrieved Mar. 6, 2018).
Maurer, Dr. Richard, "HOMA-IR: What it is & why you should know yours," The Blood Code, Sep. 20, 2016, <https://www,thebloodcode.com/homa-ir-know/.
Nah et al., "Annals of Laboratory Medicine, Comparison of Urine Albumin-to-Creatinine Ratio (ACR) between ACR strip test and quantitative test in Prediabetes and Diabetes," Jan. 2017.
Clinitek Advantus Analyzer, Siemens, Operators Guide, Jun. 2006.
Sulochana et al., "Effect or oral supplementation of free amino acids in type 2 diabetic patients—a pilot clinical trial," Medical Science Monitor.
Healthy Care Australia, Product Label for Super Lysine Cold Sore Relief, <http://healthycare.com.au/index.php/our-products/all-products/item/hc-super-lysine-cold-sore-relief-100-tablets>.
Chen, English machine translation of CN101642468.
Hirabayashi, English machine translation of WO 2008/120797.
Zhu, English machine translation of CN 102772215.
Jayawardena et al., "Effects of zinc supplementation on diabetes mellitus: a systematic review and meta-analysis." Diabetology & Metabolic Syndrome, 2012, pp. 1-15, <http://www.nbci.nlm.nih/gov/pmc/articles/PMC3407731/>.

| Categories | Triglyceride level (mg/dL) |
|---|---|
| Normal | $\leq 150$ |
| Borderline High | 150–199 |
| High | 200–499 |
| Very High | $\geq 500$ |

*FIG. 7*

METHOD OF IMPROVING BETA CELL FUNCTION USING A SUPPLEMENT

RELATED APPLICATIONS

This application is a divisional of U.S. patent application Ser. No. 16/153,450, filed on Oct. 5, 2018, which is a continuation-in-part of U.S. patent application Ser. No. 15/817,574, filed on Nov. 20, 2017, which claims the benefit of U.S. Provisional Patent Application No. 62/581,573, filed on Nov. 3, 2017, all contents of which are incorporated herein by reference in their entireties.

FIELD OF THE INVENTION

The present disclosure is generally related to improving insulin resistance and beta cell function, and more specifically, embodiments of the present disclosure relate to improving insulin resistance and beta cell function using supplements including lysine and zinc, which may also help reduce higher levels of triglycerides and/or glycated hemoglobin and help prevent advanced glycation end products (AGEs).

BRIEF SUMMARY OF THE EMBODIMENTS

Embodiments of the disclosure are directed to systems and methods for improving insulin resistance and beta cell function.

In one embodiment, a method of improving insulin resistance by using a supplement includes: administering the supplement including lysine, zinc, and vitamin C to a user; monitoring an insulin resistance level before and after the supplement is administered in a bio-sample; and determining a change in a dose of the supplement based on the insulin resistance level found in the bio-sample.

In some embodiments, the supplement includes a range of about 500 mg to about 3000 mg of lysine.

In some embodiments, the supplement further includes a range of less than about 200 mg of zinc.

In some embodiments, the supplement further includes a range of less than about 500 mg of vitamin C.

In embodiments, the supplement includes a range of about 500 mg to about 3000 mg of lysine, a range of about 10 mg to about 60 mg of zinc, and less than about 500 mg of vitamin C.

In embodiments, the lysine includes D-lysine.

In some embodiments, the lysine includes L-lysine.

In embodiments, the bio-sample is a blood sample.

In some embodiments, the method further includes displaying, on a graphical user interface of an electronic device, the insulin resistance level.

In embodiments, the method further includes providing a notification, via the electronic device, regarding a precise dosage of supplement to be administered.

In some embodiments, the notification includes a pop-up, a vibration, or a noise.

In embodiments, determining the change in the dose includes using a visual test to qualitatively determine an effectiveness of the supplement.

In one embodiment, a method of improving beta cell function by using a supplement includes: administering the supplement including lysine, zinc, and vitamin C to a user; monitoring an insulin resistance level before and after the supplement is administered in a bio-sample; and determining a change in a dose of the supplement based on the insulin resistance level found in the bio-sample.

In some embodiments, the supplement includes a range of about 500 mg to about 3000 mg of lysine, a range of about 10 mg to about 60 mg of zinc, and less than about 500 mg of vitamin C.

In embodiments, the bio-sample is a blood sample.

In some embodiments, the method may further include displaying, on a graphical user interface of an electronic device, the insulin resistance level.

In one embodiment, a method of inhibiting hepatological and pancreatic diseases using a supplement including: measuring a current triglyceride level of a user from a test; determining the current triglyceride level; and if the triglyceride level exceeds a threshold value, administering the supplement to the user including lysine.

In embodiments, the method may further include: measuring a second triglyceride level after administering the supplement; and if the second triglyceride level exceeds a threshold, administering another supplement including lysine.

In embodiments, the supplement further includes zinc and vitamin C.

In embodiments, the supplement includes a range of about 500 mg to about 3000 mg of lysine, less than about 200 mg of zinc, and less than about 500 mg of vitamin C.

BRIEF DESCRIPTION OF THE DRAWINGS

The present disclosure, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention.

FIG. 7 is a table illustrating the relationship between a category of triglyceride levels and the related triglyceride levels, consistent with embodiments disclosed herein.

Figure 1:
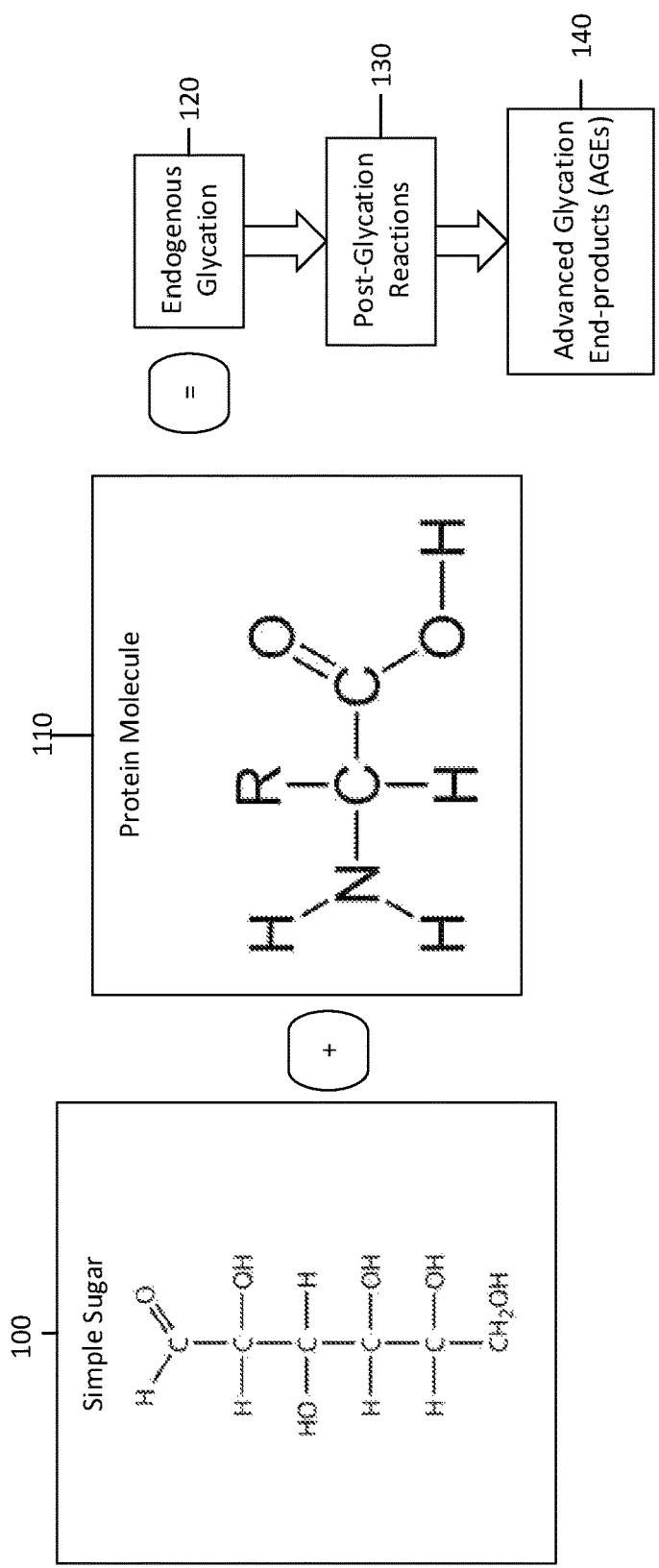
FIG. 1 is a diagram illustrating an example of endogenous glycation, consistent with embodiments disclosed herein.

These figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

The present disclosure is directed towards treatment of insulin resistance, beta cell function, liver disease, pancreas, and blood disorders using supplements including lysine and zinc. In some embodiments, the supplements may include vitamin C as well. More specifically, embodiments disclosed herein are directed towards methods for detecting the effectiveness of the supplements in improving insulin resistance and beta cell function. The supplements may compete with existing protein and lipid molecules settled within the body to reduce the number of glycated proteins and triglyceride levels and to prevent AGEs. It can be demonstrated that the supplements may interact with simple sugars that might otherwise interact with existing protein to create glycated proteins and AGEs that lead to various chronic health problems, such as lowered insulin resistance and/or beta cell function, liver disease (e.g., non-alcoholic fatty liver disease (NAFLD), hepatic steatosis, etc.), pancreatitis, and/or blood disorders. In one example, the supplement may include a range of about 500 mg to about 3000 mg of lysine, a range of about 5 mg to about 200 mg of zinc, and a range of about 50 mg to about 500 mg of vitamin C. In other embodiment, the ranges of lysine, zinc, or vitamin C may be different. One or more supplements may be taken in a day. The effectiveness of the supplements may be measured through a bio-sample, such as blood test for hemoglobin A1c, triglycerides, and/or other analytes. It has been determined that the inclusion of zinc significantly increases the efficacy of a supplement containing only lysine. The inclusion of zinc allows for the reduction in dosage/pill size with same or better results. Vitamin C may further improve insulin resistance and/or beta cell function. The inclusion of vitamin C may also further reduce the effects of diabetes, CKD, pancreatic disease, blood disorders, and liver disease.

Glycation is the bonding of a simple sugar to a protein or lipid molecule. Glycation may be either exogenous (i.e., outside the body) or endogenous (i.e., inside the body). Endogenous glycation mainly occurs in the bloodstream to absorbed simple sugars, such as glucose, fructose, and galactose. Glycation is the first change of these molecules in a slow multi-step process which leads to advanced glycation end products (AGEs). Because AGEs are irreversible end products of a glycation process, stopping the glycation process before AGEs form is important. AGEs may be benign, but many are implicated in many age-related chronic diseases such as liver disease, pancreas disease, diabetes, blood disorders, cardiovascular diseases, Alzheimer's disease, cancer, chronic kidney disease, atherosclerosis, peripheral neuropathy, and other sensory losses such as deafness. Preventing this process may also help regulate blood sugar levels of people with diabetes. It may also help regulate and/or lower triglyceride levels.

FIG. 1 is a diagram illustrating an example of endogenous glycation. As illustrated in FIG. 1, the absorbed simple sugars 100 may include glucose. As is known in the art, the simple sugars may also include fructose and galactose. Fructose experiences up to ten times the amount of glycation activity compared to glucose. As an example, FIG. 1 illustrates the structural formula for glucose. Simple sugar 100 may interact with a protein molecule 110 resulting in endogenous glycation 120. As an example, the general structural formula for an amino acid is also illustrated in FIG. 1. Various other proteins may interact with the simple sugar 100. In another embodiment, various lipid molecules may interact with the simple sugar 100. In particular, with endogenous glycation, the covalent bonding between simple sugar 100 and protein molecule 110 may occur without the control of an enzyme. Endogenous glycation occurs mainly in the bloodstream.

Glycation 130 may be a first step before these new molecules undergo post glycation reactions 140, such as Schiff base and Amadori reactions. For example, the aldehyde group of a glucose molecule may combine with the amino group of a L-lysine molecule, from a protein molecule, to form a Schiff base. In essence, a double bond may be formed between the glucose's carbon atoms and the lysine's nitrogen atoms. The Amadori product rearranges the formation of the Schiff base. As a result, AGEs 150 may be formed. For example, when an Amadori product may be oxidized, AGEs 150 are formed. While some AGEs are benign, others may contribute to liver disease, pancreatitis, blood disorders, cardiovascular disease, kidney disease, cancer, and other chronic diseases, as well as reduced insulin resistance and/or beta cell function.

Figure 2:
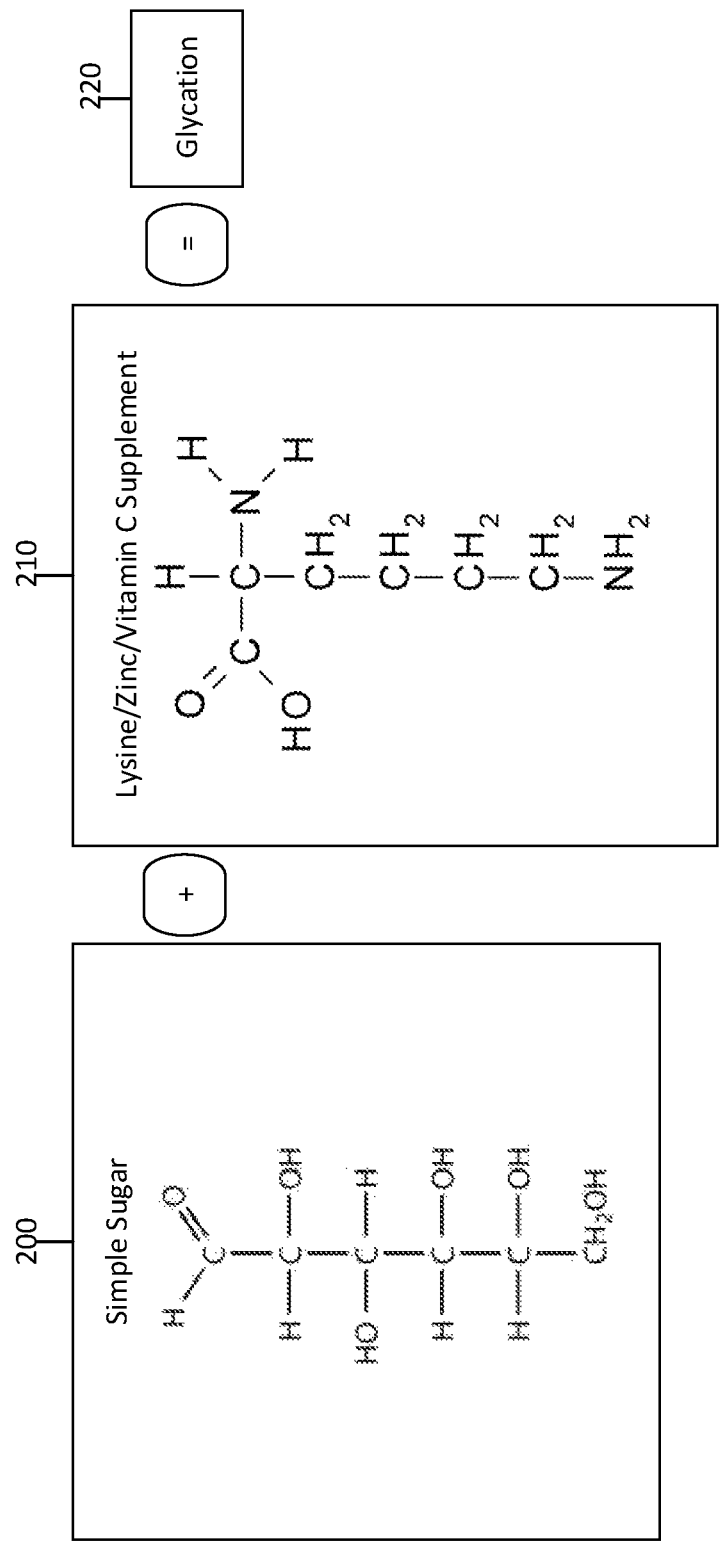
FIG. 2 is a diagram illustrating an example of glycation occurring with a supplement including lysine and zinc, consistent with embodiments disclosed herein.

FIG. 2 is a diagram illustrating an example of glycation occurring with a supplement including lysine and zinc. In this case, the simple sugars 200 interact with the supplement 210 instead of the protein molecule 110. As described above, Schiff bases form when the amino group of a lysine molecule, which is a part of a protein molecule, covalently bond with the aldehyde group of a glucose molecule. However, when a supplement including lysine is administered, the aldehyde group of a glucose molecule may bind to the lysine instead of the lysine molecule portion of the protein molecule. The supplement may include D-lysine or L-lysine. Glycation 220 may occur, but AGEs are prevented from occurring within the body, and glycated hemoglobin may be reduced. Even if Amadori products occur and AGEs form, they are not introduced into the body because the glycated lysine may be harmlessly removed through the urine. As set forth herein, it has been determined that the inclusion of zinc significantly increases the efficacy of a supplement including lysine, thereby allowing for a significant reduction in dosage/pill size with same or better results. In some embodiments, a dietary supplement may include a combination of lysine, zinc, and other nutritional supplements, e.g., vitamin C, vitamin B12, vitamin E, or other nutritional supplements. For example, a dietary supplement including lysine and vitamin C may improve immune system functionality, lower glucose levels, and reduce triglyceride levels.

Figure 3:
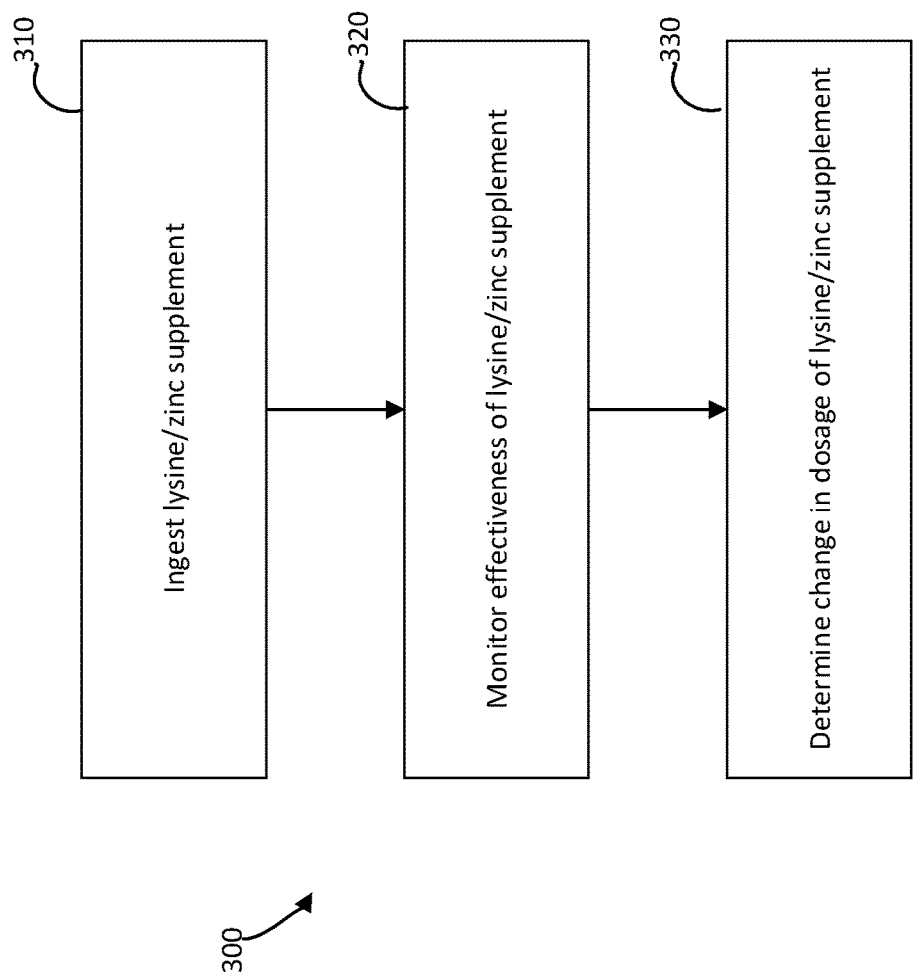
FIG. 3 is a flow chart illustrating an example method of monitoring the effectiveness of supplements including lysine and zinc from a bio-sample, consistent with embodiments disclosed herein.

FIG. 3 is a flow chart illustrating an example method of monitoring the effectiveness of supplements from a bio-sample 300. For example, method 300 may include administering a supplement including lysine and zinc at step 310. In some embodiments, the supplement may also include vitamin C. The supplement may be administered in a pill, gummy, tablet, shake, capsule, liquid extract, drink, or nutritional bar medium. The supplement may also come in various other mediums. The lysine portion of the supplement may be D-lysine or L-lysine. D-lysine, is not naturally produced within the body, and has similar chemical characteristics to L-lysine. Simple sugars may interact with D- and L-lysine in in lieu of free amino groups in structural proteins within the system. L-lysine occurs naturally in the body. Naturally occurring L-lysine may be a side-chain residue of ingested protein. L-lysine may have a bitter and/or sweet taste, making it more suitable for particular supplement mediums.

Method 300 may also include monitoring the effectiveness of the supplement at step 320. In some embodiments, effectiveness of the lysine treatment may be monitored by analyzing blood and/or urine samples. The glycated lysine may harmlessly pass through the urine upon interacting with simple sugars. A urine sample may be obtained and analyzed using a fructosamine test that measures glycated lysine. In other embodiments, a urine sample and/or a blood sample can be analyzed using a visual test. For example, some urine tests may expose the urine sample to a reagent which causes a color change indicating the concentration range of lysine within the urine or a triglyceride level in blood. A first color may indicate a healthy level of lysine in the urine or triglycerides in the blood. A healthy level of lysine may depend on the amount of lysine that is glycated, the number of supplements taken, and a given user. A healthy level of triglycerides may be less than about 150 mg/dL, but it should be appreciated that what is healthy for a particular user may vary. A second color may indicate an unhealthy level of lysine in the urine or triglycerides in the blood. An unhealthy amount of lysine may be low, indicating not much lysine was glycated. An unhealthy amount of lysine may be above 500 mg/dL, but it should be appreciated that the values may vary based on a user. It should be appreciated that more than two colors may be used to increase the granularity of the test.

In some embodiments, a more precise test may be used to indicate quantitative levels of glycated lysine in the urine sample. In addition, the urine sample may also be used to monitor blood sugar control, particularly useful for people with diabetes. As the supplement interacts with sugar, less hemoglobin may be glycated as a result. As a result, blood glucose levels, HbA1c levels, and/or triglyceride levels may decrease.

In another embodiment, the lysine concentration may be monitored using an automatic reader. For example, an optical reader on a smartphone may be used to capture the lysine concentration measurements or triglyceride levels taken on a test. An optical reader may include a camera on a smartphone. The measurement may be captured by the optical reader using the test where the glycated lysine concentration or triglyceride levels were measured. In some embodiments, the value may be manually input into the automatic reader. An optical reader may capture the measurement and transmit the measurement to a data store. Depending on this value, the automatic reader may provide notifications on whether supplements are appropriate to administer. The notification may include a pop-up, a vibration, or a noise. The notifications may continue over time. The period between notifications may increase over time. The notifications may be stopped by user input. As more data is stored, a more precise dosage of supplements may be determined to be taken over a period of time.

Method 300 may also include determining any change in the dosage of the supplement, if necessary, as in step 330. In one embodiment, a visual cue test may help determine whether more or less supplements may need to be taken. In another embodiment, a specific value on a test may indicate whether more or less lysine supplements should be taken.

Figure 4:
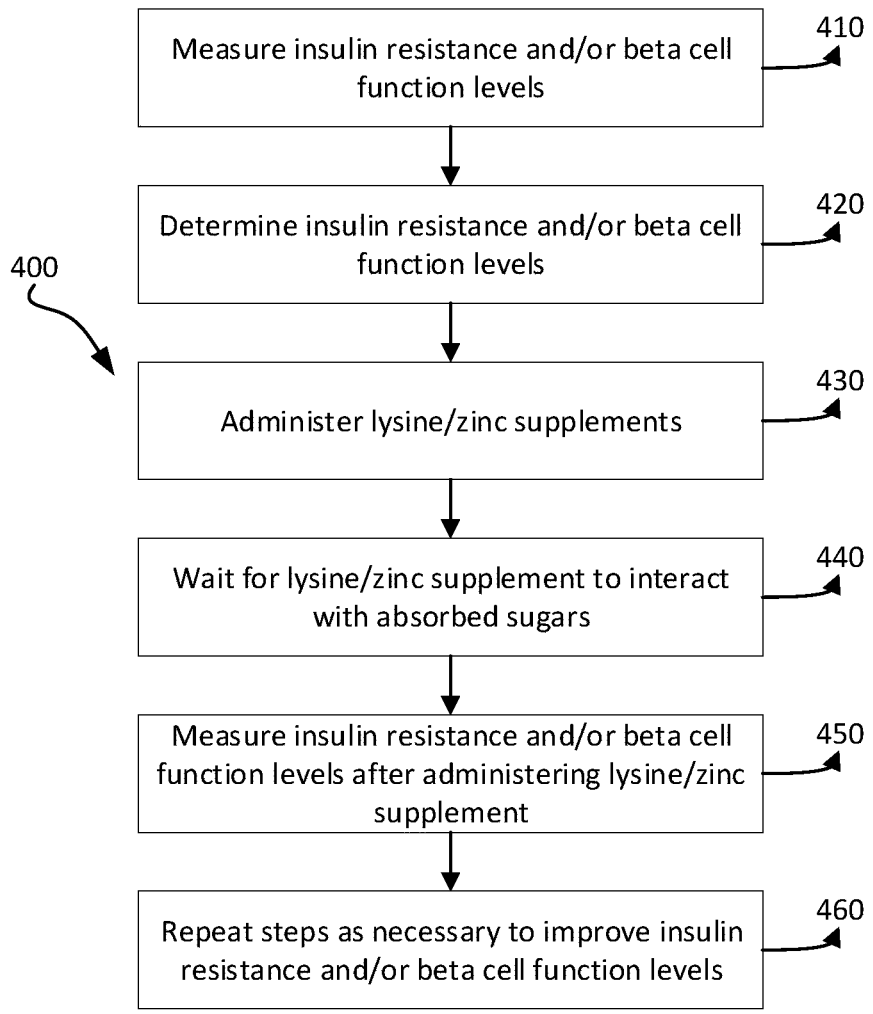
FIG. 4 is a flow chart illustrating an example method of improving insulin resistance and beta cell function using supplements including lysine, zinc, and vitamin C, consistent with embodiments disclosed herein.

FIG. 4 is a flow chart illustrating an example method of improving insulin resistance and beta cell function using supplements including lysine, zinc, and vitamin C, consistent with embodiments disclosed herein. For example, method 400 may include measuring a current insulin resistance level and/or a beta cell function level from a test at step 410. For example, the supplement may include a range of about 500 mg to about 3000 mg of lysine, a range of about 5 mg to about 200 mg of zinc, and a range of about 50 mg to about 500 mg of vitamin C. In other embodiments, the ranges of lysine, zinc, or vitamin C may be different. In still other embodiments, the supplement may include lysine and zinc, lysine and vitamin C, lysine, zinc, and vitamin C, and/or other combinations. The test may include a finger-prick test that quantitatively indicates an insulin resistance level and/or a beta cell function level. Insulin resistance levels and/or beta cell function levels may also be measured using a mid-IR device. The test may include a urine test that quantitatively indicates an insulin resistance level and/or a beta cell function level.

Method 400 may also include determining the current insulin resistance level and/or a beta cell function level at step 420. In some embodiments, a fasting plasma sample may be used to extract an insulin level, a glucose level, a c-peptide level, and/or other levels. Using the insulin resistance level and/or beta cell function level measurement from step 410, it may be determined that the insulin resistance level and/or beta cell function level is too high. A methodology used to calculate insulin resistance may be the Homeostatic Model Assessment of Insulin Resistance (HOMA-IR). Generally, levels less than about 1.0 may indicate insulin-sensitivity, an optimal level. Levels above about 1.9 may indicate early insulin resistance. Levels above about 2.9 may indicate significant insulin resistance. A methodology to calculate beta cell function may be the HOMA-β. A healthy person should have HOMA-β values around 100%. Values less than about 100% may indicate increasingly poor beta cell function. It should be appreciated that these levels vary by individuals, by race, by gender, by age, by weight, etc.

Method 400 may also include administering supplements, based on the insulin resistance level and/or beta cell function level at step 430. If the insulin resistance level and/or beta cell function level is too high, it may be appropriate to administer the supplements. The supplement may be administered in a pill, gummy form, tablet, powder for a shake, capsule, liquid extract, drink, or nutritional bar medium. The supplement may also come in various other mediums. The appropriate dosage will depend on the measured insulin level and/or beta cell function level. In some embodiments, the method may begin at step 430, where an insulin resistance level and/or beta cell function level has already passed a threshold value, as described above.

Method 400 may also include waiting for lysine to interact with absorbed sugars at step 440. After administering the supplement, a period of time should pass to allow the supplement to interact with the sugar. Method 400 may also include measuring an insulin resistance level and/or a beta cell function level after administering the supplement at step 450. After the appropriate period of time, the insulin resistance level and/or beta cell function level may be tested again to monitor any changes before and after the supplement was taken. If the insulin resistance level and/or beta cell function level is within an appropriate range, no more supplements may need to be taken. Method 400 may also include repeating the above steps as necessary to reduce an insulin resistance level and/or beta cell function level at step 460. If the measured insulin resistance level and/or beta cell function level taken after the supplement is not within an appropriate range, additional supplements may need to be taken to reduce insulin resistance levels and/or beta cell function levels.

Figure 5:
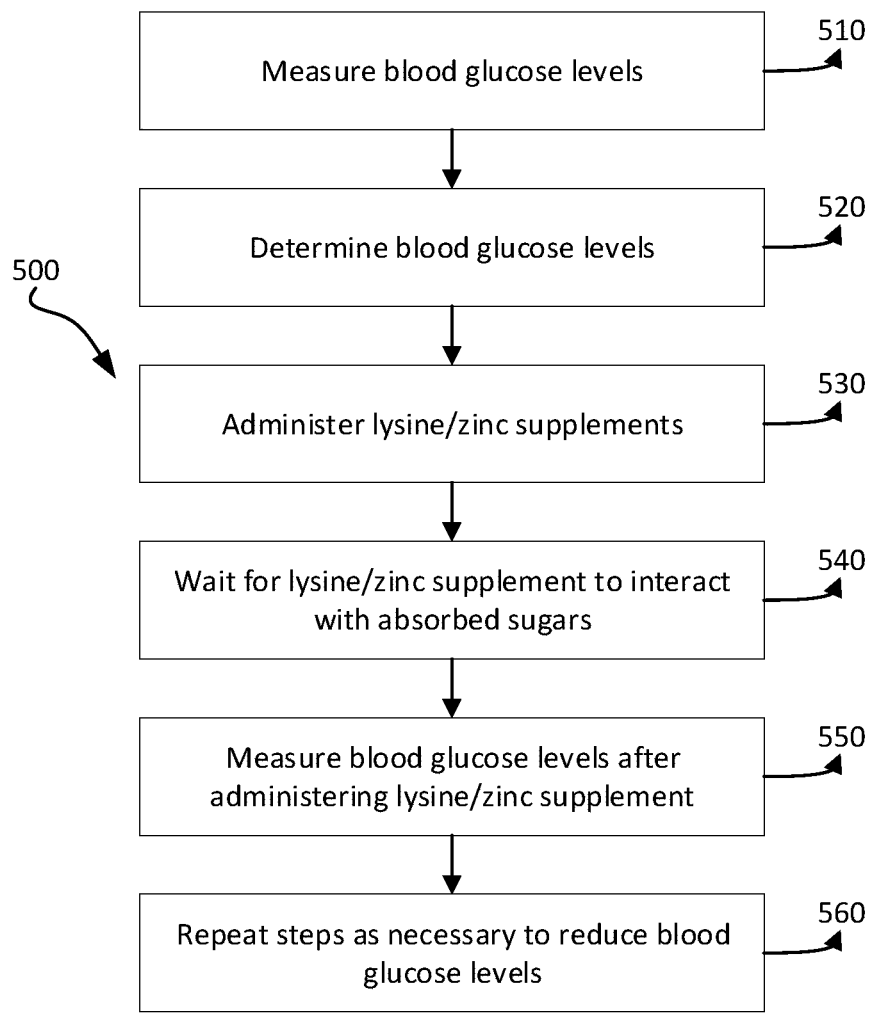
FIG. 5 is a flow chart illustrating an example method of treating diabetes using supplements including lysine, zinc, and vitamin C, consistent with embodiments disclosed herein.

FIG. 5 is a flow chart illustrating an example method of treating diabetes, liver disease, blood disorders, and/or pancreatic disease using supplements including lysine and zinc

500. In some embodiments, the supplement may also include vitamin C. For example, method 500 may include measuring the current blood glucose level from a test at step 510. In one example, the supplement may include a range of about 500 mg to about 3000 mg of lysine, a range of about 5 mg to about 200 mg of zinc, and a range of about 50 mg to about 500 mg of vitamin C. In other embodiments, the ranges of lysine, zinc, or vitamin C may be different. In still other embodiments, the supplement may include lysine and zinc, lysine and vitamin C, lysine, zinc, and vitamin C, and/or other combinations. The test may include a fingerprick test that quantitatively indicates a blood glucose level. Method 500 may also include determining blood glucose level at step 520. Using the blood glucose level measurement from step 510, it may be determined that the blood glucose level is too high. Method 500 may also include administering the supplements, based on blood glucose level at step 530. If the blood glucose level is too high, it may be appropriate to administer the supplements. The supplement may be administered in a pill, gummy form, tablet, powder for a shake, capsule, liquid extract, drink, or nutritional bar medium. The supplement may also come in various other mediums. The appropriate dosage will depend on the measured blood glucose level.

Method 500 may also include waiting for lysine to interact with absorbed sugars at step 540. After administering the supplement, a period of time should pass to allow the supplement to interact with the sugar. Method 500 may also include measuring blood glucose level after administering supplement at step 550. After the appropriate period of time, the blood glucose level may be tested again to monitor any changes before and after the supplement was taken. If blood glucose levels are within an appropriate range, no more supplements may need to be taken. Method 500 may also include repeating the above steps as necessary to reduce blood glucose levels at step 560. If the measured blood glucose level taken after the supplement is not within an appropriate range, additional supplements may need to be taken to reduce blood glucose levels.

Figure 6:
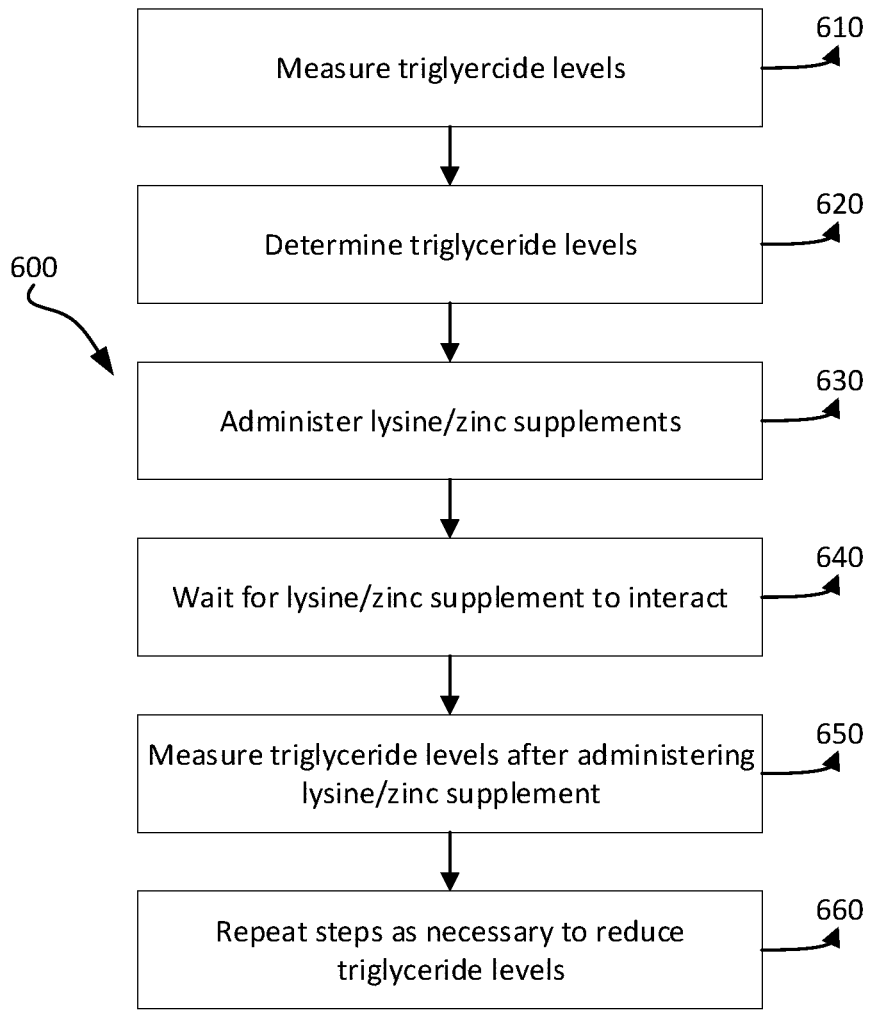
FIG. 6 is a flow chart illustrating an example method of inhibiting the effect of hepatological, pancreatic, and blood diseases using supplements including lysine, zinc, and vitamin C, consistent with embodiments disclosed herein.

FIG. 6 is a flow chart illustrating an example method of inhibiting the effect of hepatological and pancreatic diseases using supplements including lysine, zinc, and vitamin C, consistent with embodiments disclosed herein. For example, method 600 may include measuring a current triglyceride level from a test at step 610. For example, the supplement may include a range of about 500 mg to about 3000 mg of lysine, a range of about 5 mg to about 200 mg of zinc, and a range of about 50 mg to about 500 mg of vitamin C. In other embodiments, the ranges of lysine, zinc, or vitamin C may be different. In still other embodiments, the supplement may include lysine and zinc, lysine and vitamin C, lysine, zinc, and vitamin C, and/or other combinations. The test may include a fingerprick test that quantitatively indicates a triglyceride level. Triglyceride levels may also be measured using a mid-IR device. The test may include a urine test that quantitatively indicates a triglyceride level.

Method 600 may also include determining the current triglyceride level at step 620. Using the triglyceride level measurement from step 610, it may be determined that the triglyceride level is too high. Method 600 may also include administering supplements, based on the triglyceride level at step 630. If the triglyceride level is too high, it may be appropriate to administer the supplements. The supplement may be administered in a pill, gummy form, tablet, powder for a shake, capsule, liquid extract, drink, or nutritional bar medium. The supplement may also come in various other mediums. The appropriate dosage will depend on the measured triglyceride level. For some patients, a triglyceride level below about 150 mg/dL may be healthy. A triglyceride level between about 150 and about 199 mg/dL may be approaching high levels of triglycerides. Patients with high triglyceride levels may have triglyceride levels between about 200 and about 299 mg/dL. Very high triglyceride levels may be above about 500 mg/dL. It should be appreciated that these values may vary based on a given user. FIG. 7 more clearly illustrates the categories of triglyceride levels.

Method 600 may also include waiting for lysine to interact with absorbed sugars at step 660. After administering the supplement, a period of time should pass to allow the supplement to interact with the sugar. Method 600 may also include measuring a triglyceride level after administering the supplement at step 660. After the appropriate period of time, the triglyceride level may be tested again to monitor any changes before and after the supplement was taken. If the triglyceride level is within an appropriate range, no more supplements may need to be taken. Method 600 may also include repeating the above steps as necessary to reduce a triglyceride level at step 660. If the measured triglyceride level taken after the supplement is not within an appropriate range, additional supplements may need to be taken to reduce triglyceride levels.

Figure 8:
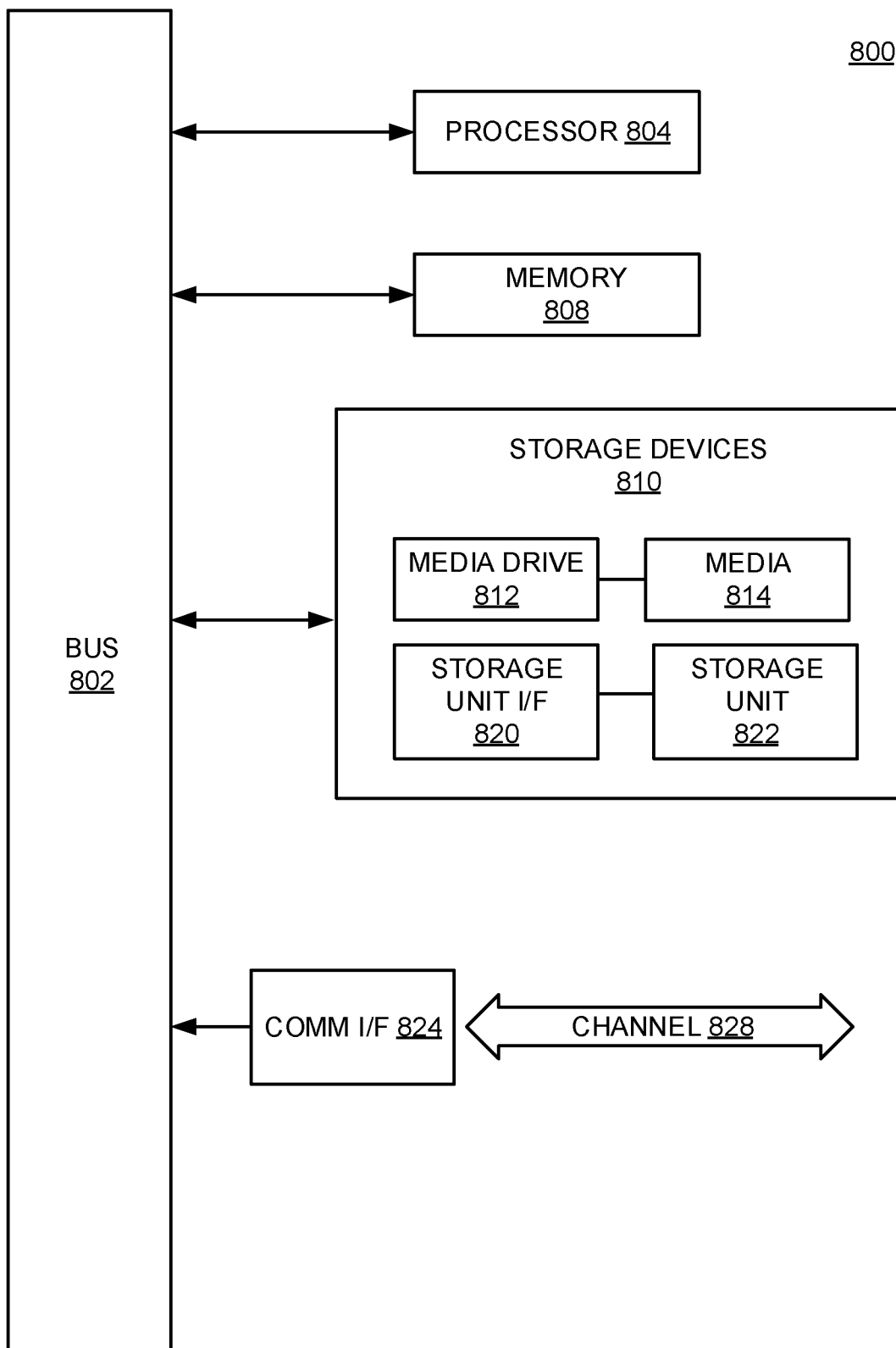
FIG. 8 is a diagram illustrating an exemplary computing module that may be used to implement any of the embodiments disclosed herein.

As used herein, the terms logical circuit and engine might describe a given unit of functionality that may be performed in accordance with one or more embodiments of the technology disclosed herein. As used herein, either a logical circuit or an engine might be implemented utilizing any form of hardware, software, or a combination thereof. For example, one or more processors, controllers, ASICs, PLAs, PALs, CPLDs, FPGAs, logical components, software routines or other mechanisms might be implemented to make up a engine. In implementation, the various engines described herein might be implemented as discrete engines or the functions and features described may be shared in part or in total among one or more engines. In other words, as would be apparent to one of ordinary skill in the art after reading this description, the various features and functionality described herein may be implemented in any given application and may be implemented in one or more separate or shared engines in various combinations and permutations. Even though various features or elements of functionality may be individually described or claimed as separate engines, one of ordinary skill in the art will understand that these features and functionality may be shared among one or more common software and hardware elements, and such description shall not require or imply that separate hardware or software components are used to implement such features or functionality.

Where components, logical circuits, or engines of the technology are implemented in whole or in part using software, in one embodiment, these software elements may be implemented to operate with a computing or logical circuit capable of carrying out the functionality described with respect thereto. One such example logical circuit is shown in FIG. 8. Various embodiments are described in terms of this example logical circuit 800. After reading this description, it will become apparent to a person skilled in the relevant art how to implement the technology using other logical circuits or architectures.

Referring now to FIG. 8, computing system 800 may represent, for example, computing or processing capabilities found within desktop, laptop and notebook computers; hand-held computing devices (PDA's, smart phones, cell phones, palmtops, etc.); mainframes, supercomputers, workstations or servers; or any other type of special-purpose or general-purpose computing devices as may be desirable or appropriate for a given application or environment. Logical circuit 800 might also represent computing capabilities embedded within or otherwise available to a given device. For example, a logical circuit might be found in other electronic devices such as, for example, digital cameras, navigation systems, cellular telephones, portable computing devices, modems, routers, WAPs, terminals and other electronic devices that might include some form of processing capability.

Computing system 800 might include, for example, one or more processors, controllers, control engines, or other processing devices, such as a processor 805. Processor 805 might be implemented using a general-purpose or special-purpose processing engine such as, for example, a microprocessor, controller, or other control logic. In the illustrated example, processor 805 is connected to a bus 802, although any communication medium may be used to facilitate interaction with other components of logical circuit 800 or to communicate externally.

Computing system 800 might also include one or more memory engines, simply referred to herein as main memory 808. For example, preferably random access memory (RAM) or other dynamic memory, might be used for storing information and instructions to be executed by processor 805. Main memory 808 might also be used for storing temporary variables or other intermediate information during execution of instructions to be executed by processor 805. Logical circuit 800 might likewise include a read only memory ("ROM") or other static storage device coupled to bus 802 for storing static information and instructions for processor 805.

The computing system 800 might also include one or more various forms of information storage mechanism 810, which might include, for example, a media drive 812 and a storage unit interface 820. The media drive 812 might include a drive or other mechanism to support fixed or removable storage media 815. For example, a hard disk drive, a floppy disk drive, a magnetic tape drive, an optical disk drive, a CD or DVD drive (R or RW), or other removable or fixed media drive might be provided. Accordingly, storage media 815 might include, for example, a hard disk, a floppy disk, magnetic tape, cartridge, optical disk, a CD or DVD, or other fixed or removable medium that is read by, written to or accessed by media drive 812. As these examples illustrate, the storage media 815 can include a computer usable storage medium having stored therein computer software or data.

In alternative embodiments, information storage mechanism 810 might include other similar instrumentalities for allowing computer programs or other instructions or data to be loaded into logical circuit 800. Such instrumentalities might include, for example, a fixed or removable storage unit 822 and an interface 820. Examples of such storage units 822 and interfaces 820 can include a program cartridge and cartridge interface, a removable memory (for example, a flash memory or other removable memory engine) and memory slot, a PCMCIA slot and card, and other fixed or removable storage units 822 and interfaces 820 that allow software and data to be transferred from the storage unit 822 to logical circuit 800.

Logical circuit 800 might also include a communications interface 826. Communications interface 826 might be used to allow software and data to be transferred between logical circuit 800 and external devices. Examples of communications interface 826 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 826 might typically be carried on signals, which can be electronic, electromagnetic (which includes optical) or other signals capable of being exchanged by a given communications interface 826. These signals might be provided to communications interface 826 via a channel 828. This channel 828 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 808, storage unit 820, media 815, and channel 828. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the logical circuit 800 to perform features or functions of the disclosed technology as discussed herein.

Although FIG. 8 depicts a computer network, it is understood that the disclosure is not limited to operation with a computer network, but rather, the disclosure may be practiced in any suitable electronic device. Accordingly, the computer network depicted in FIG. 8 is for illustrative purposes only and thus is not meant to limit the disclosure in any respect.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent engine names other than those depicted herein can be applied to the various partitions.

Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "engine" does not imply that the components or functionality described or claimed as part of the engine are all configured in a common package. Indeed, any or all of the various components of an engine, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A method of improving beta cell function by using a supplement, the method comprising:
   administering the supplement consisting of lysine, zinc, and vitamin C to a user; monitoring an insulin resistance level before and after the supplement is administered in a bio-sample; and
   determining a change in a dose of the supplement based on the insulin resistance level found in the bio-sample.

2. The method of claim 1, wherein the supplement comprises a range of about 500 mg to about 3000 mg of lysine, a range of about 10 mg to about 60 mg of zinc, and less than about 500 mg of vitamin C.

3. The method of claim 1, wherein the bio-sample is a blood sample.

4. The method of claim 1, further comprising displaying, on a graphical user interface of an electronic device, the insulin resistance level.

* * * * *